(12) United States Patent
Gavriely

(10) Patent No.: US 6,383,142 B1
(45) Date of Patent: May 7, 2002

(54) SOUND VELOCITY FOR LUNG DIAGNOSIS

(75) Inventor: Noam Gavriely, Haifa (IL)

(73) Assignee: Karmel Medical Acoustic Technologies Ltd., Yokneam-Illit (IL)

(*) Notice: Subject to any disclaimer, the term of this patent is extended or adjusted under 35 U.S.C. 154(b) by 0 days.

(21) Appl. No.: 09/647,890

(22) PCT Filed: Nov. 5, 1998

(86) PCT No.: PCT/IL98/00540

§ 371 Date: Oct. 6, 2000

§ 102(e) Date: Oct. 6, 2000

(87) PCT Pub. No.: WO00/27282

PCT Pub. Date: May 18, 2000

(51) Int. Cl.[7] ............................. A61B 5/08; A61B 7/00
(52) U.S. Cl. ...................... 600/529; 600/586; 600/561
(58) Field of Search ................................ 600/529, 561, 600/586, 438

(56) References Cited

U.S. PATENT DOCUMENTS

| 4,009,616 A | * | 3/1977 | Wonn | 73/703 |
| 4,197,856 A | * | 4/1980 | Northrop | 600/453 |
| 4,326,416 A | | 4/1982 | Fredberg | |

FOREIGN PATENT DOCUMENTS

| FR | 2 299 633 A | 8/1976 | |
| WO | WO97/29687 A1 | 8/1997 | |
| WO | WO 97/29687 | * 8/1997 | A61B/7/00 |

* cited by examiner

Primary Examiner—Robert L. Nasser
Assistant Examiner—Patricia Mallari
(74) Attorney, Agent, or Firm—Fenster & Company Patent Attorneys Ltd.

(57) ABSTRACT

A method and apparatus for determining the air pressure in a lung comprises making a determination of the velocity of sound in the lung and estimating the pressure within the lung based on the determined velocity. The method also includes determining a difference in phase for sound between two positions with respect to the lung.

37 Claims, 2 Drawing Sheets

SOUND VELOCITY FOR LUNG DIAGNOSIS

FIELD OF THE INVENTION

The present invention relates in general to the analysis of the condition of the lungs, and in particular to measuring the gas pressure in lungs.

BACKGROUND OF THE INVENTION

Intrathoracic pressure during breathing is an important physiological parameter. It is used clinically to determine the effort that is generated by a patient during breathing. This effort is necessary to overcome the resistance of the airways while ambient air is moved into the respiratory zone of the lung (the alveoli) and back out. Intrathoracic pressures may be excessive during asthma attack when the airways are abnormally narrow, or during sleep when the upper airways are completely collapsed (i.e., sleep apnea) or narrowed and fluttering (i.e., snoring). Changes in gas pressure are known to be caused by various conditions in the lungs, such as increased airway resistance as caused by asthma, chronic obstructive pulmonary disease (COPD) and other conditions.

It is also important to know the intrathoracic pressure during artificial ventilation of critically ill patients. Excessive intrathoracic pressures are a common cause of pneumothorax, a potentially lethal condition in which air leaks from the lungs into the pleural space.

At any time a ratio between a pressure difference ($\Delta P$) between the airway opening to respiratory zone and a related flow (FL) is used as an estimate of airway resistance $R=\Delta P/FL$.

Several existing methods of lung pressure measurements exist. These include the body plethysmograph in which the body is enclosed in a pressurized chamber, the esophageal balloon, in which a catheter with a long and narrow balloon is inserted via the mouth or nose into the patient's esophagus, airway opening pressure measurements, which requires intubation and which is used extensively for ventilated patients.

The invasive character and the limited accuracy of most of these methods makes them unusable outside a health care environment. For example, lung pressure measure measurements cannot be made at a patient's home, nor can they be made without inconveniencing the patient such that it may be difficult for him to sleep.

SUMMARY OF THE INVENTION

One object of some preferred embodiments of his invention is to allow for non invasive measurements of gas pressure in the lungs. Preferably, gas pressure in lungs is measured indirectly, by measuring the velocity of sound propagating in and/or through the lungs.

One aspect of some preferred embodiments of the present invention relates to using breath sounds, especially tracheal breath sounds (snore or other vocalizations) for measurements of sound velocity in the lungs. Preferably, the sound velocity in and/or through lungs is measured by determining the difference in the time at which sound, generated at the onset of and/or during a respiratory event, reaches at least two distinct points on the surface of a person's chest.

Another aspect of some preferred embodiments of the present invention relates to using a sound wave externally injected into a person's chest instead of using sounds generated at the onset and/or during a respiratory event.

In preferred embodiments of the invention, the velocity is estimated from a difference in the phase of the sound at the two points. Changes in the phase indicate a change in velocity. Preferably, the phase utilized is that in a low frequency band, characteristic of sound transfer via the lungs. This is based on an observation that high frequency waves are preferentially transferred via the solid tissue and low frequency waves are preferentially transferred via the air in the lungs.

In preferred embodiments of the invention, a frequency domain transfer function is derived for sounds between the two points and rate of change of phase with frequency (slope) of the phase portion of the transfer function is used for the measurement or indication of velocity or velocity change.

In one preferred embodiment of the invention, a baseline value is determined at the start of a session (for normal breathing) and changes are used as an indication of changes in the condition of the lungs. Alternatively or additionally, the baseline values are determined in a particular session and measurements are periodically made to determine the patient's condition over a period of time of days, weeks or years. Additionally or alternatively, the velocity measurements are compared to standard measurements which are indicative of different conditions.

In preferred embodiments of the invention, the measurements are made during segments of time which may extend from 50 msec to very long time intervals, even indefinitely.

In some preferred embodiments of the invention, only changes in the velocity (or phase) are considered important. Alternatively or additionally, absolute values of velocity are determined.

In preferred embodiments of the invention, the velocity/phase measurement is calibrated by measuring the velocity (phase) during a portion of the breath cycle when there is no air flow (at this point the alveolar pressure is equal to the external pressure) and also while the patient blows into a closed tube (no flow) at which time the pressure in the tube is the same as the alveolar pressure There is thus provided, in accordance with a preferred embodiment of the invention, a method of determining the air pressure in a lung, comprising:

making a determination of the velocity of sound in the lung; and estimating the pressure within the lung based on the determined velocity.

Preferably, the method includes determining the velocity and estimating the pressure separately for each lung.

In a preferred embodiment of the invention, making a determination comprises:

determining a difference in phase for sound between two positions with respect to the lung.

There is further provided, in accordance with a preferred embodiment of the invention, a method of determining air pressure in the lung, comprising:

determining a difference in phase for sound between two positions with respect to the lung; and estimating the pressure within the lung based on the determined phase.

Preferably, the method includes determining a difference in phase separately and estimating the pressure separately for each lung.

Preferably, the phase is determined at a single frequency at which sound travels preferentially within the gas in the lung.

Preferably, the difference in phase is determined over a range of frequencies and including determining the rate of change of phase with frequency.

Preferably, the range of frequencies is characteristic of sound that travels preferentially in the air in the lung.

Preferably, the pressure is estimated based on the determined rate of change.

In a preferred embodiment of the invention, the sound is a multi-frequency sound signal. Preferably, the sound is injected into the body of a person being tested.

In a preferred embodiment of the invention, the sound is a swept sound signal.

Alternatively, the sound is a sound generated by a person being tested, for example a snore.

There is further provided, in accordance with a preferred embodiment of the invention apparatus for measuring air pressure in at least one lung comprising:

a) a first sensor operative for measuring a first phase of a sound at a first locality in a body when placed at said first locality;

b) a second sensor operative for measuring a second phase of a sound at a second locality in a body when placed at said second locality;

c) calculation circuitry that estimates the pressure based on a difference in the measured first and second phases. Preferably, a) said first sensor is adapted to be placed near the upper portion of a lung; and b) said second sensor is adapted to be placed near a lower portion of the lung.

In a preferred embodiment of the invention, the apparatus includes a sound generator adapted to be placed outboard of said first sensor, such that the first and second sensors determine said phase of a signal traveling between the generator and the second sensor.

In a preferred embodiment of the invention, the apparatus comprises a third sensor adapted to measure a third phase of sound when placed at a third locality with respect to a lung.

Preferably, said second locality is adjacent to one lung and said third locality is adjacent to a second lung.

BRIEF DESCRIPTION OF FIGURES

The invention will be more clearly understood by reference to the following description of preferred embodiments thereof read in conjunction with the accompanying figures. Identical structures, elements or parts that appear in more than one of the figures are labeled with the same numeral in all the figures in which they appear.

DETAILED DESCRIPTION OF PREFERRED EMBODIMENTS

Figure 1:
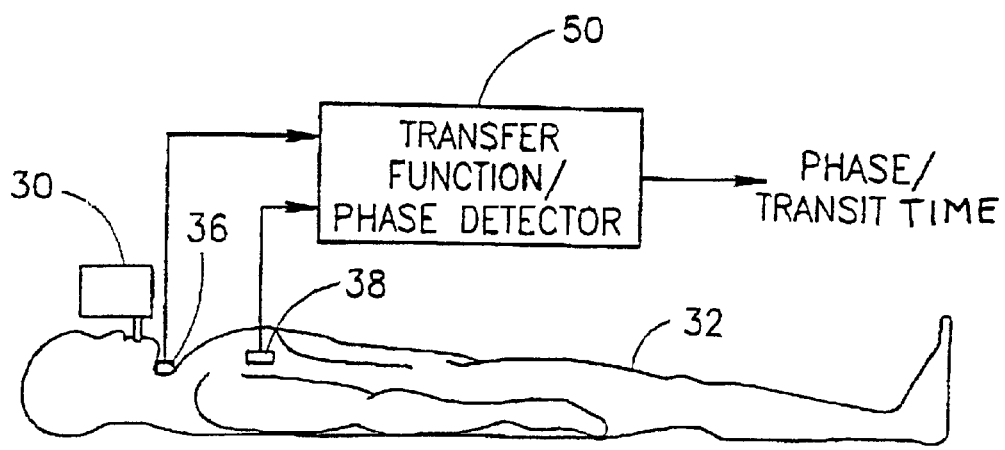
FIG. 1 shows schematically a preferred embodiment according to the invention, for generating a φ-f transfer function of the lungs, using a sound generator and two sensors.

FIG. 1 schematically shows a preferred embodiment for measuring sound velocity in lungs according to a preferred embodiment of the present invention. A sound generator 30, which generates, sound waves injects sound into a person's airways, preferably via his mouth (as shown) or nose or by applying the sound source to the wall of the person's chest 32.

Sound generated by generator 30 is injected into the upper airways and propagates downward through chest 32. A first sensor 36 is brought in contact with the chest at a point B, preferably over the trachea on the neck or in the upper chest. A second sensor 38, is brought in contact with the chest at a point C, preferably in the lower chest. Sound generated by sound generator 30 are first sensed by sensor 36, and then sensed by sensor 38, such that the difference between the sounds detected by the sensors is representative of transfer of sound between points B and C.

In some preferred embodiments of the invention, the sound generated by generator 30 is a single tone or narrow band sound. More preferably, the sound is a relatively broadband sound signal. Alternatively, the sound may be a swept audio signal.

Preferably the sound sensed by sensors 36 and 38 is input to a computing system which, utilizing information on the distance between the sensors, determines the velocity of the sound. In one preferred embodiment of the invention, the velocity of the sound is determined directly from the times of arrival of the sound at the two sensors. This may be determined by cross-correlation between the two sounds when a single frequency is generated at one time (single frequency or swept). The time delay of the cross-correlation peak represents the transit time. Furthermore, filtration of the sensed sounds may be used to reduce the effects of noise. Typical time delays are in the range of 1–5 msec. Typically, measurements are made at about 500 Hz at which the resolution of the time is accurate enough but the frequency is low enough to avoid phase ambiguity. Higher or lower frequencies may be used depending on the on the distance, the pressure changes and the required resolution.

More preferably, especially when the sound used is noise (preferably band limited to frequencies in which the sound travels preferentially via the lungs) or internally generated sounds, the velocity is determined by a measurement of the phase difference between the two sensed signals as described below.

Figure 2:
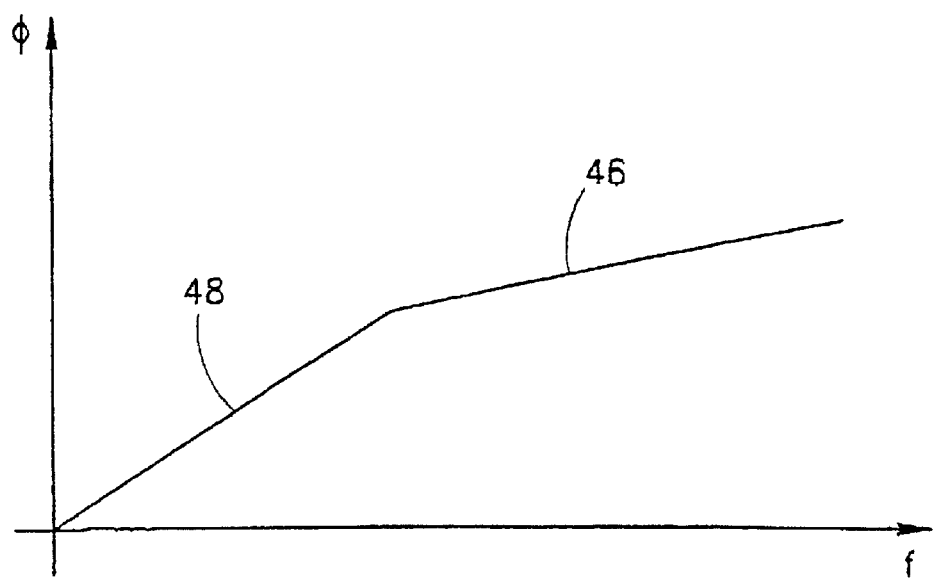
FIG. 2. shows an exemplary graph representing a φ-f transfer function for the human lungs.

A phase difference φ, exists between the detection of the sound by sensors 36 and 38. Phase φ is a function of the frequency of the sound and is dependent on the composition of the medium in which the sound propagates. By varying the frequency of sound pulses generated by sound generator 30, and by determining the phase of the sound sensed by sensors 36 and 38, a transfer function, which relates a phase φ to the pulse frequency, for sound traveling between B and C may be constructed. In some preferred embodiments of the invention, the rate of change of phase with velocity is determined. This rate of change is related to a velocity of the sound by the formula: $v=2\pi d(f/\phi)$, where d is the distance between the two sensors and $\phi/f$ is the slope of the curve. An exemplary graph representing a φ-f transfer function for the lungs is shown in FIG. 2. A first portion 46, of the graph corresponds to sound propagating in tissue while a second portion 48, corresponds to sound propagating in the lungs. A relatively sharp break situated, generally at about 300–800 Hz, of the transfer function is used to differentiate between sound that propagates in lungs from sound that propagates in tissue.

Figure 4:
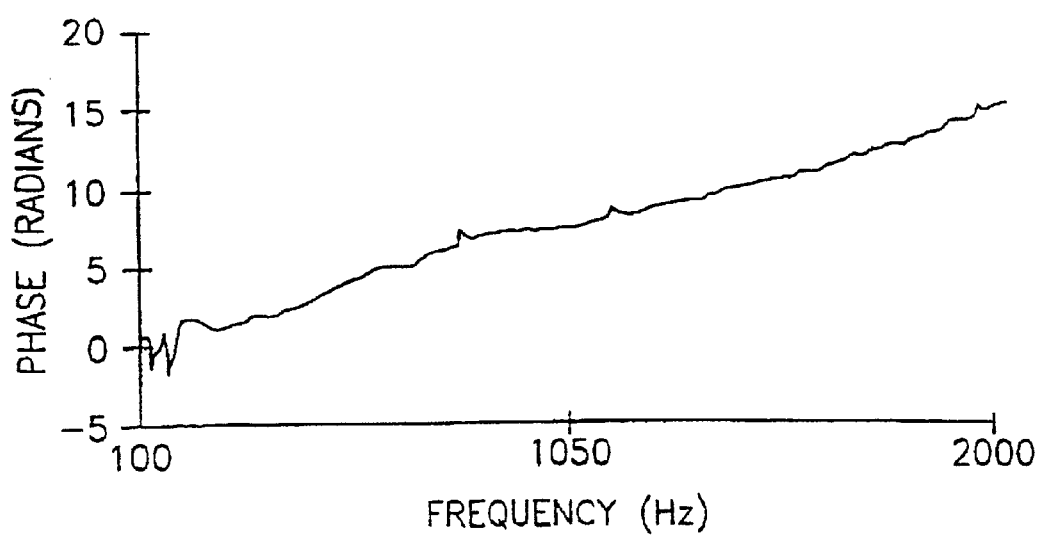
FIG. 4 is a graph of a φ-f transfer function of a human subject.

While it is generally less convenient to use the slope of this graph than a measurement at a single frequency for the determination of velocity, since determining the slope requires a broadband measurement of phase. However, the preferred broadband measurement results in more accurate results as can be noted from FIG. 4, which is a$\phi$-f transfer function, generated when a patients lungs are at a pressure of 20 cm of water using noise as the sound source. It should be noted that when noise is used as the source, the coherence of the signals is preferably verified (i.e., greater than 0.7) to assure that it is the transit time that is actually being measured.

Figure 3:
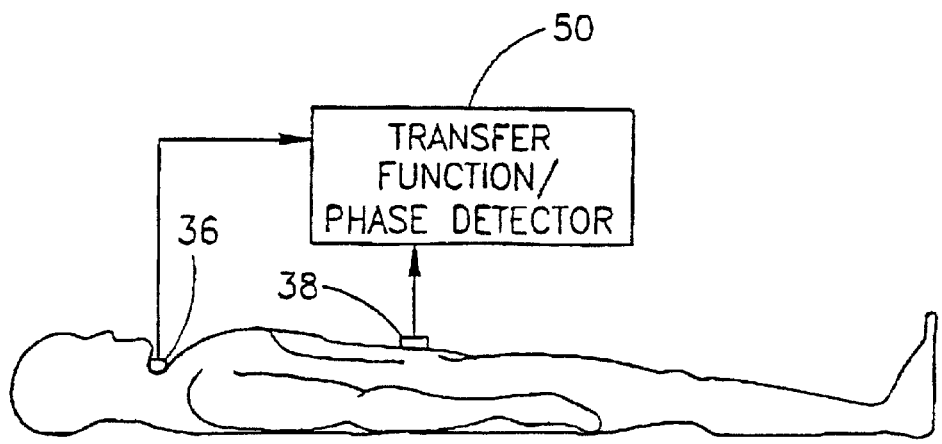
FIG. 3 shows schematically a preferred embodiment of the invention, for generating a φ-f transfer function using sound generated by a person whose lungs are being tested.

In some preferred embodiments of the present invention, instead of using a sound externally injected into the respiratory system as described above, the sound used to generate the $\phi$-f transfer function is a sound generated in the upper airways (e.g. snore) of a person whose lungs are to be diagnosed. FIG. 3 schematically shows a preferred embodiment of the invention, for $\phi$-f transfer function generation using sound generated by a person whose lungs are to be tested. A first sensor 36, is positioned on the surface of a person's chest at a point B near the neck. A second sensor 38, is positioned on the surface of a person's lower chest at a point C. The $\phi$-f transfer function generation procedure is similar to that described above.

For either embodiment of the invention, two sensors 38, can be used, one on each side of the lower chest of a person. This arrangement enables generation of two transfer functions, one for each of the two lungs.

Wave propagation speed (c) in a medium is proportional to the square root of the ratio between its Bulk Modulus (B=−V(dp/dV), is the response of a gas to a pressure change)) and density ($\rho$). In gas the bulk modulus is a product of the gas pressure (P) and the adiabatic compression coefficient ($\gamma$). This can be expressed mathematically as:

$$c = \sqrt{\frac{E}{\rho}} = \sqrt{\frac{\gamma \cdot P}{\rho}}$$

Rearranging term it is possible to obtain an expression for the pressure if the composition of the gas mixture is known:

$$P = \frac{\rho \cdot c^2}{\gamma}$$

Since $\rho$ is also dependent on the pressure, the changes in wave propagation speeds in pure gas are small and require very accurate measuring devices.

The speed of sound in open or closed cell foams or spongy materials such as the lung parenchyma is dominated by the elastance of the gas alone and the density of the composite material. Thus, the speed in the parenchyma, $c_p$ is given by:

$$c_p = \sqrt{\frac{\gamma \cdot P}{\rho_p}} = \sqrt{\frac{\gamma \cdot P}{\left(\frac{\rho_{air} \cdot V_{air} + \rho_{tissue} \cdot V_{tissue}}{V_p}\right)}}$$

where $\rho_{air}$ is the density of air, $\rho_{tissue}$ is the density of the tissue component of the parenchyma (approximately 1.0 gm/cm$^3$). $V_p$, $V_{air}$ and $V_{tissue}$ are, respectively, the volumes of the parenchyma and the air and tissue components of the parenchyma Since $V_p = V_{air} + V_{tissue}$, it is possible to substitute $V_p - V_{air}$ for $V_{tissue}$. In addition, both the air density and volume in the parenchyma are dependent on the pressure as follows:

$$\rho_{air} = \frac{\rho_{0air} \cdot P}{P_{atm}}; \quad V_{air} = V_{0air} \cdot \left(\frac{P_{atm}}{P}\right)^{\gamma},$$

where $\rho_{Oair}$ and $V_{Oair}$ are the density and parenchymal air volume under standard BTPS conditions, respectively. Substituting these expressions into (4) we obtain:

$$c_p = \sqrt{\frac{\gamma \cdot P}{\left(\rho_{tissue} - \frac{V_{0air}}{V_p} \cdot \left(\frac{P_{atm}}{P}\right)^{\gamma}\right) \cdot \left(\rho_{tissue} - \frac{\rho_{0air} \cdot P}{P_{atm}}\right)}}.$$

The transit time of sound in the parenchyma ($t_p$) is equal to the distance traveled in the parenchyma ($L_p$) divided by the speed:

$$t_p = L_p / c_p.$$

This expression can be used to determine the pressure P from the delay (phase angle) in arrival time of a wave introduced at one end of the parenchyma as shown below. However, there is a second component of time delay in a practical measurement. This component is contributed by the passage of sound through the airways $$(t_{aw} = L_{aw} / c_{air} = L_{aw} \div \sqrt{\frac{\gamma \cdot P_{atm}}{\rho_{0air}}},$$

where $L_{aw}$ is the distance traveled through air in the lung airways. Note that $t_{aw}$ is a constant with respect to changes in pressure. The total transit time t is thus given by $t = t_{aw} + t_p$. Typical parameter values for an adult are:

| Parameter | Value | Units |
|---|---|---|
| $\rho$tissue | 1 | g/cm$^3$ |
| $\gamma$ | 1.4 | |
| V$_{Oair}$ | 3000 | cm$^3$ |
| V | 4000 | cm$^3$ |
| P$_{atm}$ | 1.013*10$^6$ | g-cm/s$^2$/cm$^2$ |
| Law | 25 | cm |
| L$_p$ | 5 | cm |
| P0air | 0.0012 | g/cm$^3$ |

It should be noted that the time measured (or determined) is actually based on the sound velocity (and transit time) in the air passages and in the parenchyma and not in a single homogeneous volume. Furthermore, the volume of the air passages and the parenchyma change during the cycle. Therefore, it is desirable to precede the measurement of P by a series of measurements of time of transit during which P and lung volume are measured independently. From these measurements, a calibration curve may be obtained for a subject and later used to determine the pressure from transit time (or transit phase) measurements. These preliminary measurements can also be used to estimate the volumes of the air passages and parenchyma. These parameters nay be important in the diagnosis, follow-up and management of patients with parenchymal changes such as emphysema, fibrosis and pulmonary congestion. The calculation of the parameters is performed by taking measurements with at least four values of P, thus obtaining a matrix of four nonlinear equations in which $L_{aw}$, $L_p$, $V_{Oair}$ and $V_p$ are unknown. These equations are solved to obtain the parameter values.

The volume of air in the lung and the volume of the parenchyma ($V_{air}$ and $V_p$) change during breathing. The above discussion assumes quasi-steady state conditions. However, since $V_{0air}$ and $V_p$ influence the measured values of t and therefore the calculated values of P, changes in lung volume are preferably continuously monitored during the measurement. This may be done by integration of a flow variable (for example, using a spirometer) or by Respitrace®, magnetometers or similar devices.

While the invention has been described with reference to certain preferred embodiments, various modifications will be readily apparent to and may be readily accomplished by persons sidled in the art without departing from the spirit and the scope of the above teachings. Therefore, it is understood that the invention may be practiced other than as specifically described herein without departing from the scope of the claims hereafter.

In the claims each of the verbs, "comprise" and "include" and conjugates thereof are used to convey that the object or objects of the verb are not necessarily a listing of all the components, elements or parts of the subject or subjects of the verb.

What is claimed is:

1. A method of determining air pressure in the lung, comprising:
   determining a difference in phase for sound between two positions with respect to the lung; and
   estimating the pressure within the lung based on the determined phase difference.

2. A method according claim 1, and including determining a difference in phase separately and estimating the pressure separately for each lung.

3. A method according to claim 1, wherein the phase is determined at a single frequency at which sound travels preferentially within the gas in the lung.

4. A method according to claim 1, wherein the difference in phase is determined over a range of frequencies and including:
   determining a relationship between phase and frequency in a portion of the range.

5. A method according to claim 4, wherein the range of frequencies is characteristic of sound that travels preferentially in the air in the lung.

6. A method according to claim 4, wherein the pressure is estimated based on a determined rate of change of phase with frequency.

7. A method according to claim 1 wherein the sound is a multi-frequency sound signal.

8. A method according to claim 7, wherein the sound is injected into the body of a person being tested.

9. A method according to claim 8, wherein the sound is a swept sound signal.

10. A method according to claim 8, wherein the sound is noise.

11. A method according to claim 9 wherein the sound is band limited to include only frequencies of sound that travel preferentially through the lungs.

12. A method according to claim 7, wherein the sound is a sound generated by a person being tested.

13. A method according to claim 12 wherein the sound is a snore.

14. A method according to claim 12 wherein the sound is a tracheal sound.

15. A method according to claim 1 wherein the sound is measured between an upper portion of a lung and a lower portion of a lung.

16. Apparatus for measuring air pressure in at least one lung comprising:
   a) a first sensor operative for measuring a first phase of a sound at a first locality in a body when placed at said first locality;
   b) a second sensor operative for measuring a second phase of a sound at a second locality in a body when placed at said second locality; and
   c) calculation circuitry that estimates the pressure or a change thereof based on a difference in the measured first and second phases.

17. Apparatus according to claim 16 wherein
   a) said first sensor is adapted to be placed near the upper portion of a lung; and
   b) said second sensor is adapted to be placed near a lower portion of the lung.

18. Apparatus according to claim 16, and including a sound generator adapted to be placed outboard of said first sensor, such that the first and second sensors determine said phase of a signal traveling between the generator and the second sensor.

19. Apparatus according claim 16 and comprising a third sensor adapted to measure a third phase of sound when placed at a third locality with respect to a lung.

20. Apparatus according to claim 19 wherein said second locality is adjacent to one lung and said third locality is adjacent to a second lung.

21. A method of determining the air pressure in a lung, comprising:
   making a determination of the velocity of sound in the lung; and
   estimating the pressure within the lung based on the determined velocity.

22. A method according to claim 1 and including determining the velocity and estimating the pressure separately for a second lung.

23. A method according to claim 1 wherein making a determination comprises:
   determining a difference in phase for a sound traveling between two positions with respect to the lung.

24. A method according to claim 23 and including determining a difference in phase separately and estimating the pressure separately for each lung.

25. A method according to claim 23, wherein the phase is determated at a single frequency at which sound travels preferentially within the gas in the lung.

26. A method according to claim 23 wherein the phase is determined over a range of frequencies and including:
   determining a relationship between phase and frequency in a portion of the range.

27. A method according to claim 26 wherein the range of frequencies is characteristic of sound that travels preferentially in the air in the lung.

28. A method according to claim 26 wherein the pressure is estimated based on a determined rate of change of phase with frequency.

29. A method according to claim 1 wherein the sound is a multi-frequency sound signal.

30. A method according to claim 29 wherein the sound is injected into the body of a person being tested.

31. A method according to claim 30 wherein the sound is a swept sound signal.

32. A method according to claim 30 wherein the sound is noise.

33. A method according to claim 31 wherein the sound is band limited to include only frequencies of sound that travel preferentially through the lungs.

34. A method according to claim 29 wherein the sound is a sound generated by a person being tested.

35. A method according to claim 34 wherein the sound is a snore.

36. A method according to claim 34 wherein the sound is a tracheal sound.

37. A method according to claim 1 wherein the sound is measured between an upper portion of a lung and a lower portion of a lung.

* * * * *